(12) United States Patent
Chan et al.

(10) Patent No.: US 7,662,144 B2
(45) Date of Patent: Feb. 16, 2010

(54) CATHETER SHAFT WITH IMPROVED MANIFOLD BOND

(75) Inventors: Huey Quoc Chan, San Jose, CA (US); Tina Ye, San Jose, CA (US); Lawrence Charles Alpert, Fremont, CA (US); Sean McFerran, Newark, CA (US); Roland S. Mompar, Tracy, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 210 days.

(21) Appl. No.: 10/873,585

(22) Filed: Jun. 22, 2004

(65) Prior Publication Data

US 2005/0283134 A1 Dec. 22, 2005

(51) Int. Cl.
*A61M 25/16* (2006.01)
(52) U.S. Cl. .................. 604/523; 604/533; 604/264
(58) Field of Classification Search .................. 604/43, 604/523, 533, 264
See application file for complete search history.

(56) References Cited

U.S. PATENT DOCUMENTS

| | | | |
|---|---|---|---|
| 2,185,741 A | 1/1940 | Sorg et al. |
| RE25,788 E | 6/1965 | Sheridan |
| 3,318,335 A | 5/1967 | Heller |
| 3,348,544 A | 10/1967 | Braun |
| 3,470,869 A | 10/1969 | Fenton et al. |
| 3,633,758 A | 1/1972 | Morse |
| 3,720,210 A | 3/1973 | Diettrich |
| 3,725,522 A | 4/1973 | Sheridan et al. |
| 3,752,510 A | 8/1973 | Windischman et al. |
| 3,861,972 A | 1/1975 | Glover et al. |
| 3,865,666 A | 2/1975 | Shoney |
| 3,873,391 A | 3/1975 | Plauka et al. |
| 3,914,002 A | 10/1975 | Berliner et al. |
| 3,950,052 A | 4/1976 | Walter et al. |
| 3,959,429 A | 5/1976 | Benning |
| 3,985,601 A | 10/1976 | Panagrossi |
| 3,989,571 A | 11/1976 | Harautuneian |
| 4,085,185 A | 4/1978 | Adair |
| 4,093,484 A | 6/1978 | Harrison et al. |
| 4,154,244 A | 5/1979 | Becker et al. |
| 4,171,943 A | 10/1979 | Tschanz et al. |
| 4,191,185 A | 3/1980 | Lemieux |
| 4,198,983 A | 4/1980 | Becker et al. |
| 4,207,900 A | 6/1980 | Patel et al. |
| 4,210,478 A | 7/1980 | Shoney |
| 4,284,459 A | 8/1981 | Patel et al. |
| 4,326,519 A | 4/1982 | D'Alo et al. |
| 4,328,056 A | 5/1982 | Snooks |

(Continued)

FOREIGN PATENT DOCUMENTS

EP 0 437 291 B1 7/1991

(Continued)

*Primary Examiner*—Nicholas D Lucchesi
*Assistant Examiner*—Laura A Bouchelle
(74) *Attorney, Agent, or Firm*—Crompton, Seager & Tufte, LLC

(57) ABSTRACT

A catheter shaft with an improved manifold bond and methods for making and using the same. The catheter shaft may include a sleeve disposed, for example, near its proximal end. The sleeve may include a first layer that is attached to the catheter shaft and a second layer to which a hub or manifold may be attached.

40 Claims, 7 Drawing Sheets

U.S. PATENT DOCUMENTS

| | | | |
|---|---|---|---|
| 4,354,495 A | 10/1982 | Bodicky | |
| 4,355,721 A | 10/1982 | Knott, II et al. | |
| 4,489,961 A | 12/1984 | Laidig | |
| 4,509,877 A | 4/1985 | Sobin et al. | |
| 4,511,163 A | 4/1985 | Harris et al. | |
| 4,531,943 A | 7/1985 | Van Tassel et al. | |
| 4,557,781 A | 12/1985 | Hoppie | |
| 4,592,749 A | 6/1986 | Ebling et al. | |
| 4,596,563 A | 6/1986 | Pande | |
| 4,602,808 A | 7/1986 | Herron et al. | |
| 4,607,746 A | 8/1986 | Stinnette | |
| 4,610,674 A | 9/1986 | Suzuki et al. | |
| 4,655,762 A | 4/1987 | Rogers | |
| 4,705,507 A | 11/1987 | Boyles | |
| 4,737,219 A | 4/1988 | Taller et al. | |
| 4,753,765 A | 6/1988 | Pande | |
| 4,778,550 A | 10/1988 | Barton et al. | |
| 4,802,947 A | 2/1989 | Bartholomew | |
| 4,806,182 A | 2/1989 | Rydell et al. | |
| 4,826,480 A | 5/1989 | Diaz et al. | |
| 4,838,269 A | 6/1989 | Robinson et al. | |
| 4,842,590 A | 6/1989 | Tanabe et al. | |
| 4,863,441 A | 9/1989 | Lindsay et al. | |
| 4,863,442 A | 9/1989 | DeMello et al. | |
| 4,874,373 A | 10/1989 | Luther et al. | |
| 4,875,481 A | 10/1989 | Higgins | |
| 4,886,506 A | 12/1989 | Lovgren et al. | |
| 4,950,257 A | 8/1990 | Hibbs et al. | |
| 4,959,067 A | 9/1990 | Muller | |
| 4,960,412 A | 10/1990 | Fink | |
| 4,964,409 A | 10/1990 | Tremulis | |
| 5,031,775 A | 7/1991 | Kane | |
| 5,035,686 A | 7/1991 | Crittenden et al. | |
| 5,041,095 A | 8/1991 | Littrell | |
| 5,085,645 A | 2/1992 | Purdy et al. | |
| 5,125,903 A | 6/1992 | McLaughlin et al. | |
| 5,125,913 A | 6/1992 | Quackenbush | |
| 5,129,887 A | 7/1992 | Euteneuer et al. | |
| 5,139,032 A | 8/1992 | Jahrmarkt et al. | |
| 5,143,409 A | 9/1992 | Lalikos | |
| 5,160,559 A | 11/1992 | Scovil et al. | |
| 5,167,647 A | 12/1992 | Wijkamp et al. | |
| 5,181,750 A | 1/1993 | Reum | |
| 5,190,529 A | 3/1993 | McCrory et al. | |
| 5,201,723 A | 4/1993 | Quinn | |
| 5,217,555 A | 6/1993 | Franklin, III et al. | |
| 5,221,270 A | 6/1993 | Parker | |
| 5,226,898 A | 7/1993 | Gross | |
| 5,240,537 A | 8/1993 | Bodicky | |
| 5,248,305 A | 9/1993 | Zdrahala | |
| 5,254,107 A | 10/1993 | Soltesz | |
| 5,279,596 A | 1/1994 | Castaneda et al. | |
| 5,300,032 A | 4/1994 | Hibbs et al. | |
| 5,312,356 A | 5/1994 | Engelson et al. | |
| 5,318,032 A | 6/1994 | Lonsbury et al. | |
| 5,330,444 A | 7/1994 | Webler et al. | |
| 5,330,449 A | 7/1994 | Prichard et al. | |
| 5,358,493 A | 10/1994 | Schweich, Jr. et al. | |
| 5,366,444 A | 11/1994 | Martin | |
| 5,376,077 A | 12/1994 | Gomringer | |
| 5,380,301 A | 1/1995 | Prichard et al. | |
| 5,387,193 A | 2/1995 | Miraki | |
| 5,395,332 A | 3/1995 | Ressemann et al. | |
| 5,403,292 A | 4/1995 | Ju | |
| 5,466,230 A | 11/1995 | Davila | |
| 5,484,409 A | 1/1996 | Atkinson et al. | |
| 5,507,300 A | 4/1996 | Mukai et al. | |
| 5,507,728 A | 4/1996 | Erskine | |
| 5,533,988 A | 7/1996 | Dickerson et al. | |
| 5,545,151 A | 8/1996 | O'Connor et al. | |
| 5,558,635 A | 9/1996 | Cannon | |
| 5,558,652 A | 9/1996 | Henke | |
| 5,569,218 A | 10/1996 | Berg | |
| 5,599,325 A | 2/1997 | Ju et al. | |
| 5,599,326 A | 2/1997 | Carter | |
| 5,607,055 A | 3/1997 | Bettinger | |
| 5,658,251 A | 8/1997 | Ressemann et al. | |
| 5,695,467 A | 12/1997 | Miyata et al. | |
| 5,702,439 A | 12/1997 | Keith et al. | |
| 5,725,513 A | 3/1998 | Ju et al. | |
| 5,743,875 A * | 4/1998 | Sirhan et al. | 604/96.01 |
| 5,746,701 A | 5/1998 | Noone | |
| 5,762,637 A | 6/1998 | Berg et al. | |
| 5,772,642 A * | 6/1998 | Ciamacco et al. | 604/523 |
| 5,782,797 A * | 7/1998 | Schweich et al. | 604/507 |
| 5,803,510 A | 9/1998 | Dorsey, III | |
| 5,827,242 A | 10/1998 | Follmer et al. | |
| 5,830,401 A | 11/1998 | Prichard et al. | |
| 5,867,883 A | 2/1999 | Iorio et al. | |
| 5,876,374 A | 3/1999 | Alba et al. | |
| 5,897,537 A | 4/1999 | Berg et al. | |
| 5,897,584 A | 4/1999 | Herman | |
| 5,931,812 A | 8/1999 | Andersen et al. | |
| 5,980,486 A | 11/1999 | Enger | |
| 5,984,907 A * | 11/1999 | McGee et al. | 604/525 |
| 5,993,399 A | 11/1999 | Pruitt et al. | |
| 6,027,475 A | 2/2000 | Sirhan et al. | |
| 6,033,388 A | 3/2000 | Nordstrom et al. | |
| 6,036,715 A | 3/2000 | Yock | |
| 6,042,578 A | 3/2000 | Dinh et al. | |
| 6,047,825 A | 4/2000 | Samuels | |
| 6,053,313 A | 4/2000 | Farrell et al. | |
| 6,068,121 A | 5/2000 | McGlinch | |
| 6,068,622 A | 5/2000 | Sater et al. | |
| 6,074,379 A | 6/2000 | Prichard | |
| 6,102,890 A | 8/2000 | Stivland et al. | |
| 6,156,054 A * | 12/2000 | Zadno-Azizi et al. | 606/194 |
| 6,228,073 B1 | 5/2001 | Noone et al. | |
| 6,238,376 B1 | 5/2001 | Peterson | |
| 6,264,630 B1 * | 7/2001 | Mickley et al. | 604/96.01 |
| 6,273,404 B1 | 8/2001 | Holman et al. | |
| 6,273,879 B1 | 8/2001 | Keith et al. | |
| 6,332,874 B1 | 12/2001 | Eliasen et al. | |
| 6,440,119 B1 | 8/2002 | Nakada et al. | |
| 6,475,184 B1 | 11/2002 | Wang et al. | |
| 6,475,208 B2 | 11/2002 | Mauch | |
| 6,500,157 B2 | 12/2002 | Luther | |
| 6,575,959 B1 | 6/2003 | Sarge et al. | |
| 6,585,719 B2 | 7/2003 | Wang | |
| 6,648,854 B1 | 11/2003 | Patterson et al. | |
| 6,733,487 B2 | 5/2004 | Keith et al. | |
| 2001/0016702 A1* | 8/2001 | Benjamin | 604/19 |
| 2002/0095133 A1* | 7/2002 | Gillis et al. | 604/502 |
| 2003/0093059 A1 | 5/2003 | Griffin et al. | |
| 2003/0120207 A1 | 6/2003 | Wang | |
| 2003/0152788 A1 | 8/2003 | Velliky | |

FOREIGN PATENT DOCUMENTS

| | | |
|---|---|---|
| EP | 0 761 253 A2 | 3/1997 |
| EP | 0 782 868 A1 | 7/1997 |
| EP | 0 937 480 A1 | 8/1999 |
| FR | 2092970 | 1/1972 |
| GB | 2 187 670 A | 9/1987 |
| WO | WO 99/11313 A1 | 3/1999 |
| WO | WO 03/41783 A1 | 5/2003 |

* cited by examiner

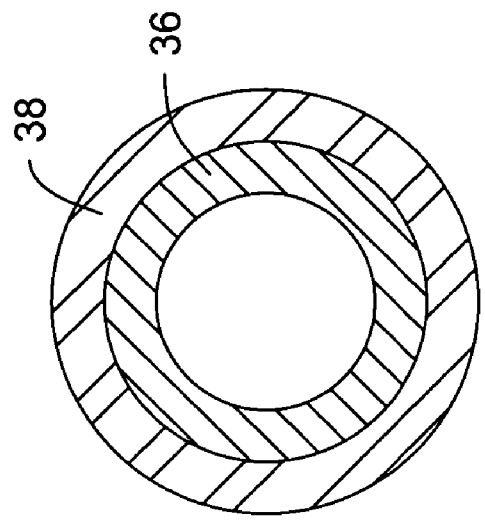
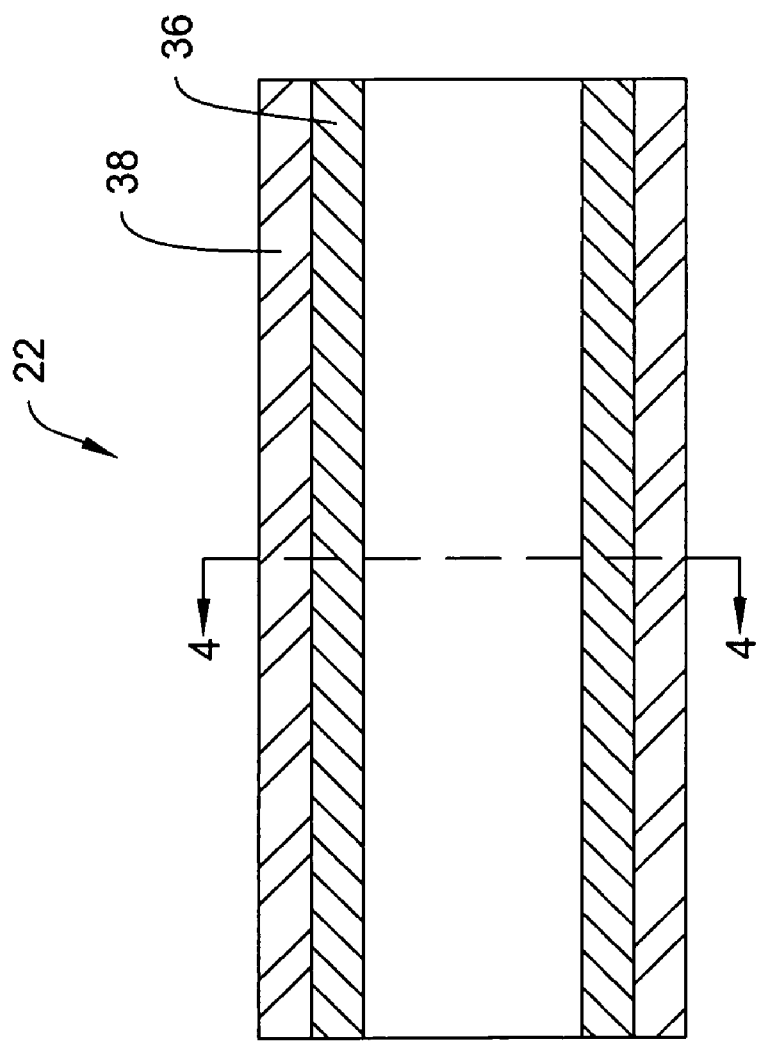
Figure 4
Figure 3

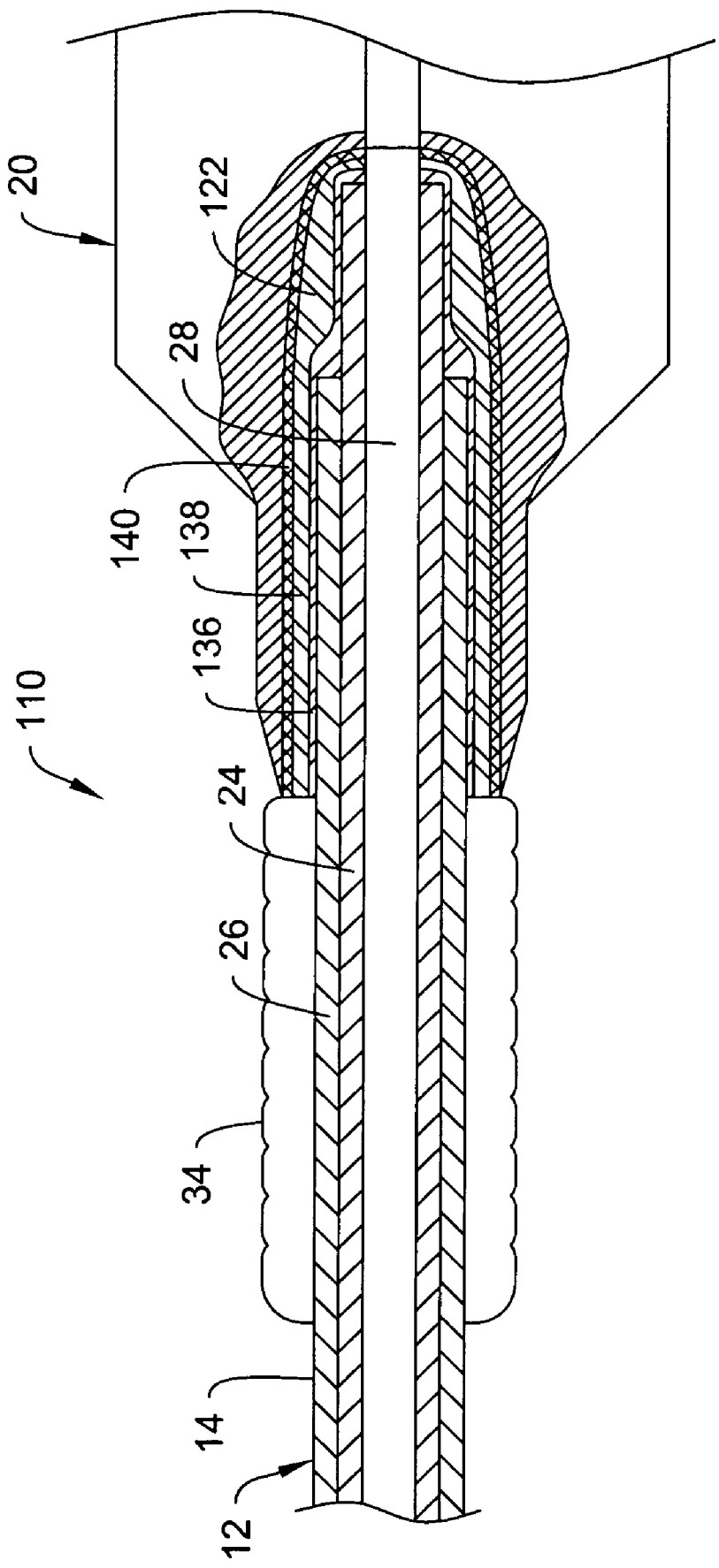

CATHETER SHAFT WITH IMPROVED MANIFOLD BOND

FIELD OF THE INVENTION

The invention relates to intraluminal medical devices, for example, intravascular catheters and catheter shafts. More particularly, the invention relates to catheter shafts with improved hub or manifold bonding.

BACKGROUND

A wide variety of intraluminal medical devices have been developed for medical use, for example, intravascular use. Some of these devices include catheters and catheter shafts that can have hubs or manifolds attached thereto. Of the known catheters and catheter shafts, each has certain advantages and disadvantages. There is an ongoing need to provide alternative designs and methods of making and using catheter shafts with desirable characteristics.

BRIEF SUMMARY

The invention provides design, material, and manufacturing method alternatives for catheters and catheter shafts. In at least some embodiments, a catheter shaft may include a proximal and a distal end region. A sleeve can be attached or otherwise affixed to the shaft adjacent the proximal end region. A hub or manifold can be attached to the catheter shaft at least in part via the sleeve. The sleeve can include multiple layers. In a preferred embodiment, one of the layers can have desirable bonding compatibility with the shaft. Another one of the layers can have desirable bonding compatibility with the hub or manifold. The use of the sleeve, therefore, can improve and facilitate the bond between the catheter shaft and the hub or manifold, particularly when a portion of the shaft is metallic.

The above summary of some embodiments is not intended to describe each disclosed embodiment or every implementation of the present invention. The Figures and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 3 is a cross-sectional side view of an example sleeve for use with a catheter;

FIG. 4 is a transverse cross-sectional view of the sleeve shown in FIG. 3;

FIG. 5 is a partial cross-sectional side view of a hub coupled to another example sleeve and a catheter shaft;

DETAILED DESCRIPTION

Figure 1:
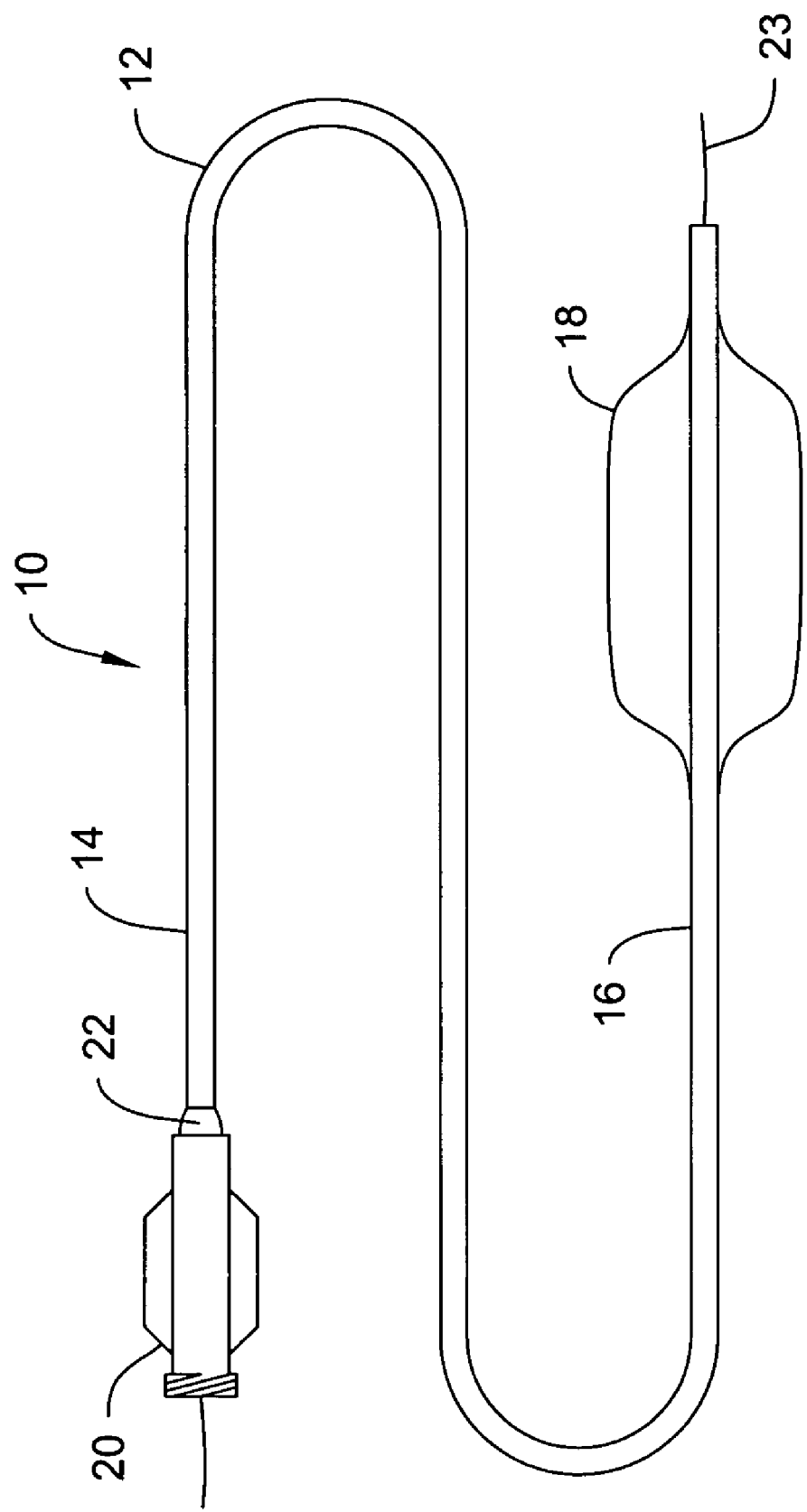
FIG. 1 is a schematic plan view of an example catheter.

The following description should be read with reference to the drawings wherein like reference numerals indicate like elements throughout the several views. The detailed description and drawings illustrate example embodiments of the claimed invention.

FIG. 1 is a plan view of an example catheter 10. Catheter 10 includes a catheter shaft 12 having a proximal end region 14 and a distal end region 16. In some embodiments, catheter 10 is a balloon catheter. According to these embodiments, a balloon 18 may be disposed adjacent distal end region 16. Catheter 10, in alternative embodiments, need not be a balloon catheter, as catheter 10 can be any suitable catheter or related medical device such as a guide catheter or diagnostic catheter. As detailed in FIG. 2, a hub or manifold 20 is disposed adjacent proximal end region 14. In a representative embodiment, a sleeve 22 is also disposed adjacent proximal end region 14. For example, sleeve 22 may be attached to proximal end region 14, and hub 20 may at least in part be attached to sleeve 22. Sleeve 22 and some of the alternative embodiments thereof are described in more detail below.

The use of catheter 10 can be similar to the use of typical catheters. For example, catheter 10 may be advanced through the vasculature of a patient over a guidewire 23 to a location adjacent a target region. Catheter 10 may then be used for its intended purpose. For example, if catheter 10 is a balloon catheter (as shown) then balloon 18 may be inflated. Inflated balloon 18 may, for example, expand a stenosis, position and/or expand an intravascular stent (not shown, but may be disposed on balloon 18), and the like, or perform any other suitable function.

Injection molding techniques have proven quite useful for forming and attaching hubs and manifolds, like hub 20, to catheter shafts, like catheter shaft 12. Some of the polymeric materials commonly used for catheter hubs, however, have been found not highly bond compatible with materials used for catheter shafts of exemplary embodiments disclosed herein. In at least some embodiments, sleeve 22 can overcome this by providing a bonding compatible contact surface for hub 20 to bond with. Accordingly, sleeve 22 is specifically designed to be sufficiently or highly bond compatible with both catheter shaft 12 and with hub 20, thereby improving the integrity of the bond. At least one of the specific designs utilized by sleeve 22 is the inclusion of multiple layers. One of the layers is configured to securely bond with catheter shaft 12, and another layer is configured to securely bond with hub 20 (i.e., hub 20 that is injection molded thereto). Some of the other features, characteristics, and design attributes of sleeve 22 are described in more detail below.

Figure 2:
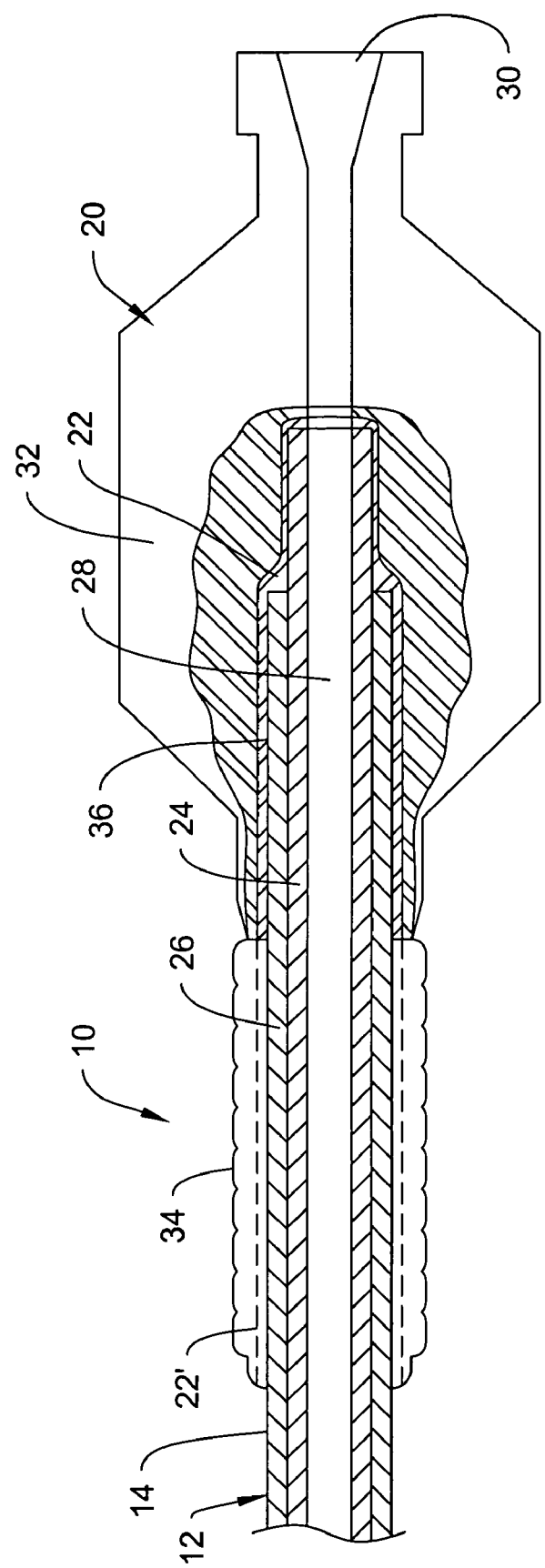
FIG. 2 is a partial cross-sectional side view of an example sleeve coupled to a catheter shaft and a hub coupled to the sleeve.

FIG. 2 is a partial cross-sectional view of catheter shaft 12 adjacent proximal end region 14 with a portion of hub 20 cut away to better show a preferred shaft/hub interface. Here it can be seen that catheter shaft 12 may include an inner tubular member 24 and outer tubular member 26. Tubular members 24/26 may be manufactured from a number of different materials. For example, tubular members 24/26 may be made of metals, metal alloys, polymers, metal-polymer composites or any other suitable materials. Some examples of suitable metals and metal alloys include stainless steel, such as 300 series stainless steel (including 304V, 304L, and 316L); 400 series martensitic stainless steel; tool steel; nickel-titanium alloy such as linear-elastic or super-elastic Nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polybutylene terephthalate (PBT), polyether block ester, polyurethane, polypropylene (PP), polyvinylchloride (PVC), polyether-ester (for example, a polyether-ester elastomer such as ARNITEL® available from DSM Engineering Plastics), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, polyethylene (PE), Marlex high-density polyethylene, Marlex low-density polyethylene, linear low density polyethylene (for example, REXELL®), polyethylene terephthalate (PET), polyetheretherketone (PEEK), polyimide (PI), polyetherimide (PEI), polyphenylene sulfide (PPS), polyphenylene oxide (PPO), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like. In some embodiments tubular members 24/26, or any other portion of catheter 10, can be blended with a liquid crystal polymer (LCP). Of course, any other polymer or other suitable material including ceramics may be used without departing from the spirit of the invention. The materials used to manufacture inner tubular member 24 may be the same as or be different from the materials used to manufacture outer tubular member 26. The inner tubular member 24 may also be a micromachined hypotube including slots, spiral cuts or some other form of aperture which gives desired bending characteristics to the hypotube. Those materials listed herein may also be used for manufacturing other components of catheter 10.

Tubular members 24/26 may be arranged in any appropriate way. For example, in some embodiments inner tubular member 24 can be disposed coaxially within outer tubular member 26. According to these embodiments, inner tubular member 24 and outer tubular member 26 may or may not be secured to one another along the general longitudinal axis of shaft 12. Alternatively, inner tubular member 24 may follow the inner wall or otherwise be disposed adjacent the inner wall of outer tubular member 26. Again, inner tubular member 24 and outer tubular member 26 may or may not be secured to one another. For example, inner tubular member 24 and outer tubular member 26 may be bonded, welded (including tack welding or any other welding technique), or otherwise secured at a bond point. In still other embodiments, inner tubular member 24 and outer tubular member 26 may be adjacent to and substantially parallel to one another so that they are non-overlapping. In these embodiments, shaft 12 may include an outer sheath that is disposed over tubular members 24/26. In still another embodiment, inner tubular member 24 may comprise a liner or lubricious coating disposed along the inner wall of outer tubular member 26.

Inner tubular member 24 may include or otherwise define an inner lumen 28. In at least some embodiments, inner lumen 28 is a guidewire lumen. Accordingly, catheter 10 can be advanced over guidewire 23 to the desired location. The guidewire lumen may extend along essentially the entire length of catheter shaft 12 so that catheter 10 resembles traditional "over-the-wire" catheters. Alternatively, the guidewire lumen may extend along only a portion of shaft 12 so that catheter 10 resembles a "single-operator-exchange" or a "rapid-exchange" catheter. Regardless of which type of catheter is contemplated, catheter 10 may be configured so that balloon 18 is disposed over at least a region of inner lumen 28. In at least some of these embodiments, inner lumen 28 (i.e., the portion of inner lumen 28 that balloon 18 is disposed over) may be substantially coaxial with balloon 18. Alternatively, inner lumen 28 may be an inflation lumen that may be used, for example, to transport inflation media to and from balloon 18.

In at least some embodiments, inner tubular member 24 extends proximally from the proximal end of outer tubular member 26. This arrangement may be desirable for a number of reasons. For example, extending inner tubular member 24 proximally from outer tubular member 26 may allow a user to gain access to a lumen (e.g., an inflation lumen) that might be defined between inner tubular member 24 and outer tubular member 26. Accordingly, hub 20 may include a first port 30 in communication with lumen 28 and a second port (not shown) in communication with the inflation lumen. Moreover, extending inner tubular member 24 proximally from outer tubular member 26 may also be desirable because it allows the position of inner tubular member 24 to be secured relative to the position of outer tubular member 26 by virtue of attaching sleeve 22 to both inner tubular member 24 and outer tubular member 26.

Hub or manifold 20 may be generally similar to other typical hubs. For example, hub 20 may be made from a polymeric material (such as polyamide, PEBA, PU, PVC, PP, PE, and the like, or any other material listed herein) and may include a flanged portion 32 exemplified by the inclusion of one, two, or more flanges. In addition, hub 20 may include a strain relief 34. Generally, strain relief 34 may ease the transition from catheter shaft 12 to hub 20. Strain relief 34 may attach to hub 20 on the distal side of hub 20 and extend distally therefrom. In some embodiments, strain relief 34 may be disposed over sleeve 22. This is illustrated in FIG. 2 by sleeve 22 being shown in phantom lines under strain relief 34. In other embodiments, strain relief 34 may not be disposed over sleeve 22 or only be disposed over a portion of sleeve 22. It can be appreciated that a number of different types, arrangements, and configurations can be utilized for strain relief 34 without departing from the spirit of the invention.

Sleeve 22 is shown in FIG. 2 with a solid line interface with hub 20. It is, however, recognized that this interface may become indistinct due to hear during assembly such as by insert molding the hub to the shaft. Further, sleeve 22 is shown as a single layer, but may include a plurality of layers. This feature is not shown in FIG. 2 but made explicit in FIGS. 3 and 4. First layer 36 may be the inner layer of sleeve 22 that is disposed over and attached to catheter shaft 12. Second layer 38 may be the outer layer of sleeve 22 that hub 20 is attached to. In some embodiments, one or more additional layers may be disposed between first layer 36 and second layer 38 or on top of or below first layer 36 and/or second layer 38. In some embodiments, sleeve 22 may function or otherwise take the form of a "tie layer" that ties together catheter shaft 12 and hub 20. Some discussion of tie layers that may be applicable to the present invention can be found in U.S. Patent Application Publication No. US 2003/0120207, the entire disclosure of which is herein incorporated by reference.

Sleeve 22 and the layers 36/38 thereof may be made from any suitable material including, for example, any of the polymers and other materials listed herein. In some embodiments, first layer 36 and second layer 38 are made from different materials. First layer 36 may be made from a material that is well suited for bonding with inner tubular member 24 (i.e., in embodiments where inner tubular member 24 extends proximally out from outer tubular member 26 or is otherwise available for bonding with sleeve 22) and outer tubular member 26. For example, first layer 36 may include a polymer manufactured by Equistar Chemical Company under the trademark PLEXAR®. PLEXAR® tie-layer resins are anhydride-modified polyolefins (or linear low-density polyethylene) that can bond to dissimilar materials such as ethylene vinyl alcohol, nylon (polyamides), polyolefins, polyethylene terephthalate (PET), polystyrene (PS), epoxy, polyurethane (PU), polyvinylidene chloride (PVdC), metal, paper, and other substrates while still providing excellent adhesion to polyethylene. Alternatively, first layer 36 may include a modified polyolefin with functional groups such as ADMER®, which is manufactured by Mitsui Chemicals. ADMER® resins can similarly bond to a variety of materials such as polyolefins, ionomers, polyamides, ethylene vinyl alcohol, PET, polycarbonates, PS, and metals. Suitable varieties include, for example, ADMER® QB520E and QB510E, available from Mitsui Chemicals. Other appropriate materials include BYNEL® (such as BYNEL® 50E571, which is available from DuPont), a mixture of Finapro PPC 2660 (e.g., about 97%) and FUSABOND® MD 353D (e.g., about 3%, which is available from DuPont), polypropylene acrylic acid copolymers like PolyBond (such as PolyBond PB 3002, which is available Uniroyal Chemicals), and the like. Materials like those listed above may be well suited for first layer 36, for example, because they bond well to both polymeric materials (including those from which inner tubular member 24 may be made) and to metal materials (from which outer tubular member 26 may be made). It can be appreciated that a number of other materials could also be used. As suggested above, second layer 38 may be made from a different material. For example, second layer 38 may be made from another polymer such as polyamide, nylon, nylon-12 (e.g., GRILAMID® TR55LX), polyether block amide, and the like, or any other suitable material including those disclosed herein. Generally, second layer 38 includes a material suitable for bonding hub 20 thereto (e.g., via injection molding).

The thickness and/or other dimensional aspects of sleeve 22 may vary. For example, first layer 36 may be from about 0.0001 to about 0.0015 inches thick. Second layer 38 may be from about 0.001 to about 0.015 inches thick. In some embodiments, the thickness of first layer 36 may be about the same as the thickness of second layer 38. In other embodiments, the thickness is different. For example, first layer 36 may be thinner than second layer 38.

Manufacturing sleeve 22 may include a co-extrusion process that defines a generally tubular sleeve 22 having first layer 36 and second layer 38. Co-extruded sleeve 22 can be disposed at a suitable location such as adjacent proximal portion 14 of catheter shaft 12. As suggested above, sleeve 22 may be disposed over a portion of both inner tubular member 24 and outer tubular member 26 as seen in FIG. 2. The properly positioned sleeve 22 can be thermally bonded to shaft 12 using standard thermal bonding techniques. Thermally bonding sleeve 22 to catheter shaft 12 includes thermally bonding first layer 36 to catheter shaft 12. Alternatively, any other suitable bonding technique may be used. As stated above, the material chosen for first layer 36 may be selected so that it can bond to both inner tubular member 24 and outer tubular member 26. In alternative embodiments, sleeve 22 can be co-extruded directly onto catheter shaft 12. Depending on the thermal conditions of the co-extrusion, this embodiment may or may not include an additional heating step to thermally bond sleeve 22 to shaft 12. Hub 22 can be attached to catheter shaft 12 by injection molding it over sleeve 22 (i.e., second layer 38) according to typical injection molding techniques.

Another example catheter 110 is shown in FIG. 5. Catheter 110 is similar in form and function as catheter 10, except that sleeve 122 includes first layer 136, second layer 138, and a third layer 140. First layer 136 and second layer 138 may be similar to the aforementioned first layer 36 and second layer 38. Third layer 140 may be made from a polymer including any of those listed herein. For example, third layer 140 may be made from polyether block amide, nylon, GRILAMID®, and the like. Third layer 140 may be fused onto the subassembly defined by co-extrusion of first layer 136 and second layer 138. In at least some embodiments, third layer 140 may be used as a heat shield to reduce melting of first layer 136, second layer 138, or any other portion of catheter 110 that might otherwise occur due to heat generated during the injection molding of hub 20 onto catheter shaft 12 or other heat-related manufacturing steps.

Figure 6:
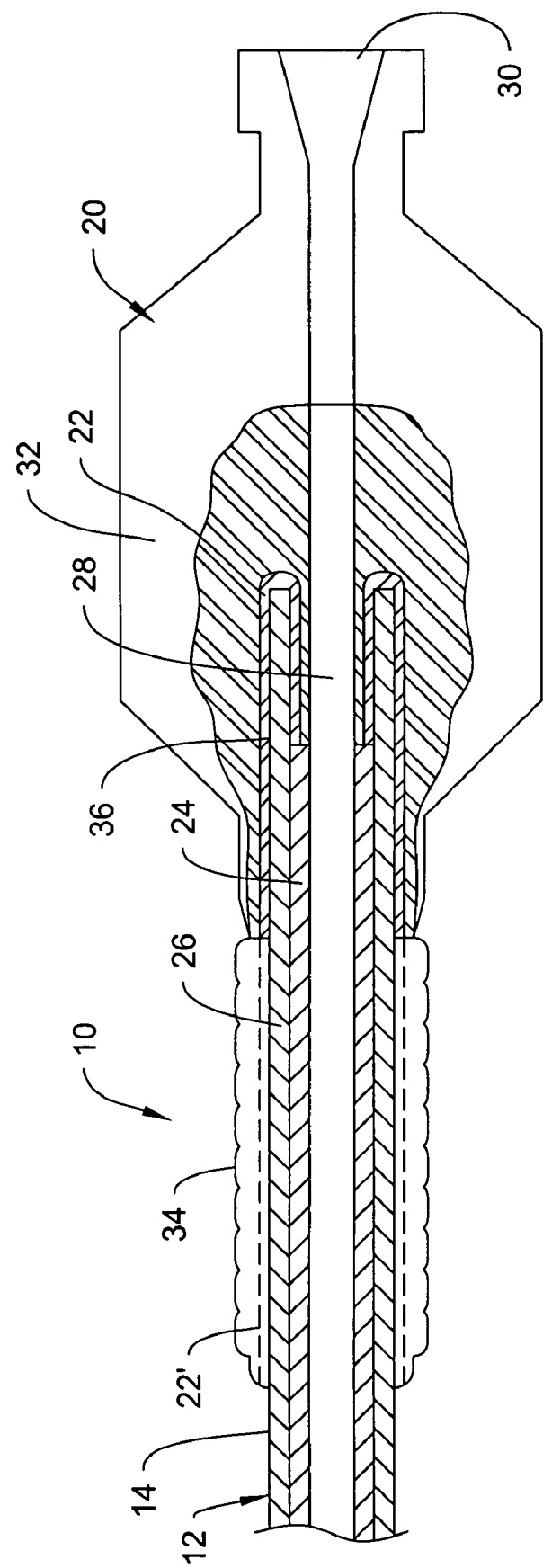
FIG. 6 is a partial cross-sectional side view of a hub coupled to another example sleeve and a catheter shaft.
Figure 7:
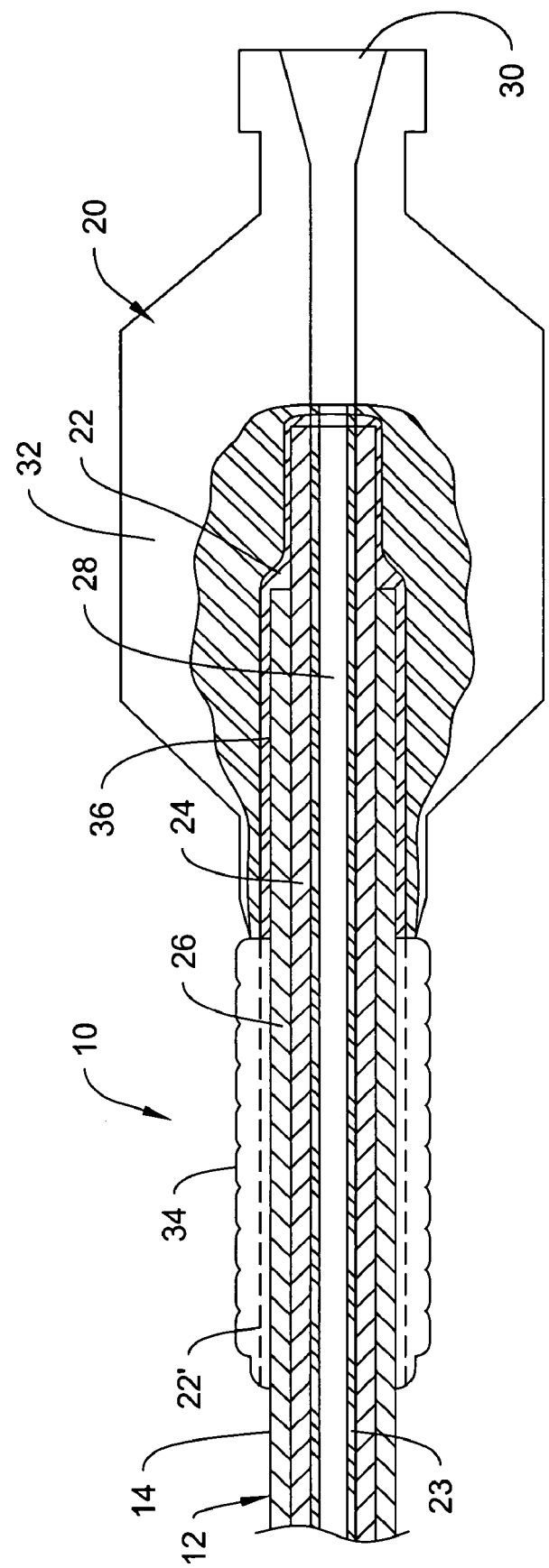
FIG. 7 is a partial cross-sectional side view of another example sleeve and a catheter shaft.
Figure 8:
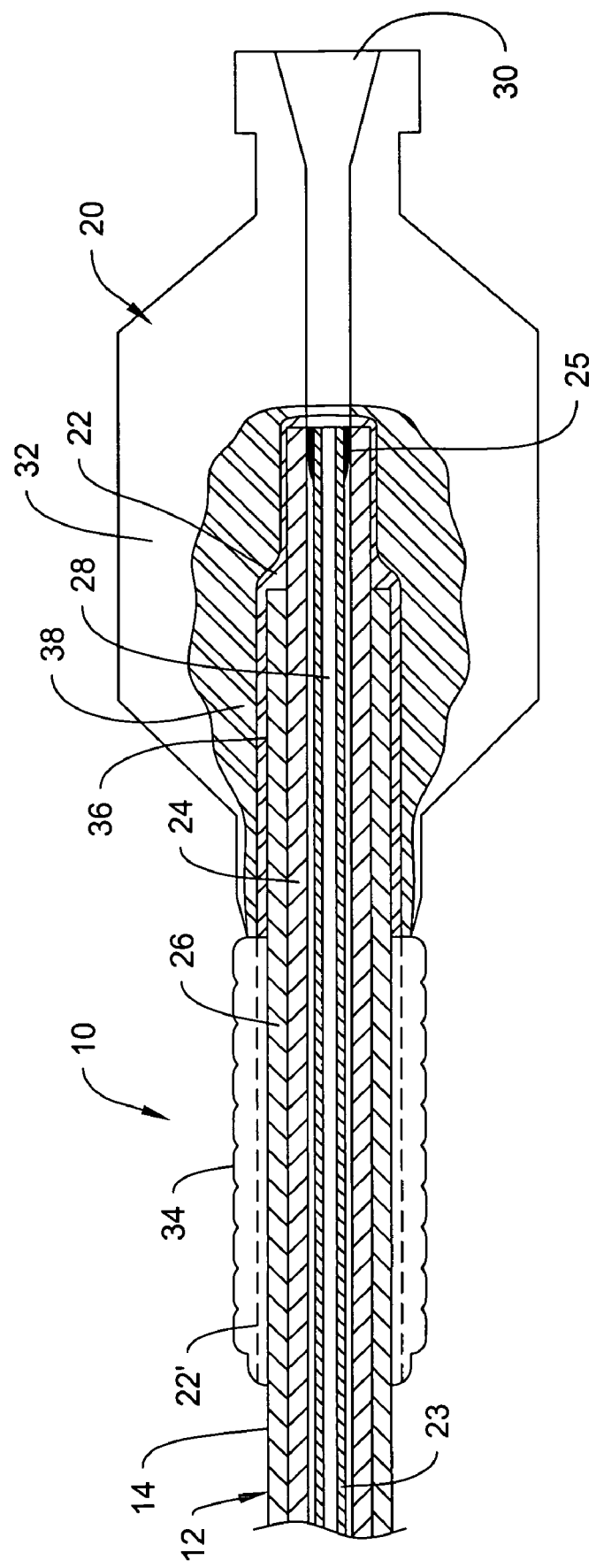
FIG. 8 is a partial cross-sectional side view of another example sleeve and a catheter shaft.

FIGS. 6, 7 and 8 show specific alternative embodiments of the present invention. In the embodiment of FIG. 6, the inner layer 24 is a metallic hypotube having an outer polymer layer 26 that extends proximally beyond the proximal end of inner layer 24. The embodiment of FIG. 7 is similar to FIG. 2 discussed above, but further includes a three-layer shaft, which can, in some embodiments, include an inner layer 23, which can be a polymer, a middle hypotube or metallic layer 24 and an outer polymeric layer 26. The embodiment of FIG. 8 also includes a three-layer shaft. However, inner layer 23 is a tubular member sized to fit within middle layer 24 while retaining an annular space therebetween. This inner layer 23 can be a hypotube or polymeric layer. The inner tube 23 is preferably attached to the middle layer 24 near its proximal end, such as by an adhesive 25.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device, comprising:
an elongate shaft including an outer tubular member and an inner tubular member disposed within the outer tubular member, the outer tubular member and the inner tubular member each having a proximal end;
wherein the proximal end of the inner tubular member extends proximally beyond the proximal end of the outer tubular member;
a first sleeve coupled to the elongate shaft adjacent the proximal ends of the inner and outer tubular members, the first sleeve including an inner layer and an outer layer disposed around the inner layer, the outer layer being different from the inner layer, the inner layer being bonded to an outer surface of the outer tubular member and bonded to an outer surface of the inner tubular member; and
a hub, wherein the outer layer of the first sleeve is bonded to an inner surface of the hub.

2. The medical device of claim 1, wherein the outer tubular member includes a metal.

3. The medical device of claim 2, wherein the outer tubular member is a nickel titanium alloy.

4. The medical device of claim 1, wherein the outer tubular member includes stainless steel.

5. The medical device of claim 1, wherein the inner tubular member includes a polymer.

6. The medical device of claim 1, wherein the outer tubular member is disposed on the outside of a hypotube and the inner tubular member is disposed on the inside of the hypotube and connected with an adhesive material.

7. The medical device of claim 6, wherein the inner tubular member ends flush with the proximal end of the hypotube.

8. The medical device of claim 6, wherein the inner tubular member ends distal to the proximal end of the hypotube.

9. The medical device of claim 1, wherein the inner layer of the first sleeve includes a material that is compatible for bonding with metal.

10. The medical device of claim 1, wherein the inner layer of the first sleeve includes a material that is compatible for bonding with stainless steel.

11. The medical device of claim 1, wherein the inner layer of the first sleeve includes a material that is compatible for bonding with polyolefins.

12. The medical device of claim 1, wherein the inner layer of the first sleeve includes a material that is compatible for bonding with nylon.

13. The medical device of claim 1, wherein the inner layer of the first sleeve includes a modified polyolefin with functional groups.

14. The medical device of claim 1, wherein the outer layer of the first sleeve includes a polymer.

15. The medical device of claim 1, wherein the outer layer of the first sleeve includes nylon.

16. The medical device of claim 1, wherein the outer layer of the first sleeve includes polyamide.

17. The medical device of claim 1, wherein the outer layer of the first sleeve includes polyether block amide.

18. The medical device of claim 1, further comprising a second sleeve disposed over and attached to the first sleeve.

19. A medical device, comprising:
a catheter shaft having a proximal end region and a distal end region;
wherein the catheter shaft includes a first tubular member and a second tubular member disposed within and extending proximally from a proximal end of the first tubular member;
a sleeve disposed at the proximal end region of the catheter shaft, the sleeve including an inner layer and an outer layer disposed around the inner layer, the outer layer being different from the inner layer, an inner surface of the inner layer bonded to an outer surface of the first tubular member and bonded to an outer surface of the second tubular member; and
a hub, wherein the outer layer of the sleeve is bonded to an inner surface of the hub.

20. The medical device of claim 19, wherein the outer tubular member is disposed on the outside of a hypotube and the inner tubular member is disposed on the inside of the hypotube and connected with an adhesive material.

21. The medical device of claim 20, wherein the inner tubular member ends flush with the proximal end of the hypotube.

22. The medical device of claim 20, wherein the inner tubular member ends distal to the proximal end of the hypotube.

23. The medical device of claim 19, wherein the first tubular member includes a metal.

24. The medical device of claim 19, wherein the second tubular member includes a polymer.

25. The medical device of claim 19, wherein the inner layer of the sleeve includes a modified polyolefin with functional groups.

26. The medical device of claim 19, wherein the outer layer of the sleeve includes nylon.

27. The medical device of claim 19, wherein the outer layer of the sleeve includes polyamide.

28. The medical device of claim 19, wherein the outer layer of the sleeve includes polyether block amide.

29. The medical device of claim 19, further comprising a second sleeve member disposed over and attached to the sleeve.

30. A method for attaching a hub to a catheter shaft, comprising the steps of:
providing an elongate catheter shaft, the shaft having a proximal end region;
providing a sleeve having an inner layer and an outer layer disposed around the inner layer, the outer layer being different from the inner layer;
wherein the inner layer is compatible for bonding with metal and the outer layer is compatible for bonding with polymers;
bonding the inner layer of the sleeve to an outer surface of the proximal end region of the elongate shaft;
providing a hub; and
bonding an inner surface of the hub to the outer layer of the sleeve.

31. The method of claim 30, wherein the inner layer of the sleeve includes a modified polyolefin with functional groups.

32. The method of claim 30, wherein the outer layer of the sleeve includes nylon.

33. The method of claim 30, wherein the outer layer of the sleeve includes polyamide.

34. The method of claim 30, wherein the outer layer of the sleeve includes polyether block amide.

35. The method of claim 30, wherein the step of attaching a sleeve to the proximal end region includes heating the sleeve.

36. The method of claim 30, wherein the step of attaching a hub to the outer layer of the sleeve includes injection molding the hub onto the outer layer of the sleeve.

37. A medical device, comprising:
an elongate catheter shaft including an outer tubular member and an inner tubular member disposed within the outer tubular member;
a sleeve disposed around and in contact with a circumferential surface of the outer tubular member and disposed around and in contact with a circumferential surface of the inner tubular member;
wherein the sleeve includes a first means for bonding with the catheter shaft; and
a hub disposed around and in contact with the sleeve;
wherein the sleeve includes a second means for bonding with the hub.

38. A method for attaching a hub to a catheter shaft, comprising the steps of:
providing an elongate catheter shaft, the shaft having a proximal end region;
providing a sleeve having an inner layer and an outer layer disposed around the inner layer, the outer layer being different from the inner layer;
thermally bonding the inner layer of the sleeve to an outer surface of the catheter shaft; and
injection molding a hub onto the outer layer of the sleeve.

39. A method for attaching a hub to a catheter shaft, comprising the steps of:

providing an elongate catheter shaft including a hypotube, the shaft having a proximal end region;
providing a sleeve having an inner layer and an outer layer disposed around the inner layer, the outer layer being different from the inner layer;
thermally bonding the inner layer of the sleeve to the hypotube of the catheter shaft; and
injection molding a hub onto the outer layer of the sleeve.

40. A medical device, comprising:

an elongate shaft including an outer tubular member and an inner tubular member disposed within the outer tubular member, the outer tubular member and the inner tubular member each having a proximal end;

wherein the proximal end of the outer tubular member extends proximally beyond the proximal end of the inner tubular member;
a first sleeve including an inner layer of a first polymeric material and an outer layer of a second polymeric material different from the first polymeric material, the outer layer disposed around the inner layer, the inner layer bonded to the outer tubular member and bonded to the inner tubular member; and
a hub, wherein the outer layer of the first sleeve is bonded to the hub.

* * * * *

UNITED STATES PATENT AND TRADEMARK OFFICE
CERTIFICATE OF CORRECTION

PATENT NO.        : 7,662,144 B2
APPLICATION NO.   : 10/873585
DATED             : February 16, 2010
INVENTOR(S)       : Chan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 259 days.

Signed and Sealed this

Thirtieth Day of November, 2010

David J. Kappos
*Director of the United States Patent and Trademark Office*